(12) United States Patent
DiCesare et al.

(10) Patent No.: US 7,758,608 B2
(45) Date of Patent: Jul. 20, 2010

(54) ENHANCED DEXTERITY SURGICAL HAND PIECE

(76) Inventors: Paul DiCesare, 68 Wells Hill Rd., Easton, CT (US) 06612; Patrick N. Gutelius, 4 Wheeler Rd., Monroe, CT (US) 06468

( * ) Notice: Subject to any disclaimer, the term of this patent is extended or adjusted under 35 U.S.C. 154(b) by 587 days.

(21) Appl. No.: 10/625,965

(22) Filed: Jul. 24, 2003

(65) Prior Publication Data
US 2004/0158233 A1 Aug. 12, 2004

Related U.S. Application Data

(60) Provisional application No. 60/398,134, filed on Jul. 25, 2002.

(51) Int. Cl.
*A61B 17/00* (2006.01)
(52) U.S. Cl. .......................... 606/205; 606/1
(58) Field of Classification Search .............. 606/1, 606/41, 46, 47, 51–52, 113, 114, 148, 170, 606/174, 205–208; D08/56–58; 600/104
See application file for complete search history.

(56) References Cited

U.S. PATENT DOCUMENTS

| | | | | |
|---|---|---|---|---|
| 4,744,147 A * | 5/1988 | Modin | ..................... | 30/254 |
| 5,147,373 A * | 9/1992 | Ferzli | ..................... | 606/144 |
| 5,261,917 A * | 11/1993 | Hasson et al. | ............... | 606/139 |
| 5,275,613 A * | 1/1994 | Haber et al. | ............... | 606/205 |
| 5,281,220 A * | 1/1994 | Blake, III | ..................... | 606/46 |
| 5,376,094 A | 12/1994 | Kline | ........................ | 606/113 |
| 5,456,684 A | 10/1995 | Schmidt et al. | ............... | 606/41 |
| 6,039,752 A * | 3/2000 | Kimura et al. | ............... | 606/205 |
| 6,066,146 A | 5/2000 | Carroll et al. | ............... | 606/148 |
| 6,258,101 B1 | 7/2001 | Blake, III | ..................... | 606/113 |
| 6,299,625 B1 | 10/2001 | Bacher | ........................ | 606/170 |
| 6,383,195 B1 | 5/2002 | Richard | ........................ | 606/114 |
| 6,394,964 B1 * | 5/2002 | Sievert et al. | ............... | 600/564 |
| 6,428,530 B1 * | 8/2002 | Matern et al. | ................. | 606/1 |
| 6,533,797 B1 * | 3/2003 | Stone et al. | ................. | 606/184 |
| 6,673,092 B1 * | 1/2004 | Bacher | ........................ | 606/205 |
| 2006/0149222 A1 * | 7/2006 | Okada | ........................ | 606/1 |

* cited by examiner

*Primary Examiner*—Michael Peffley
*Assistant Examiner*—Victoria W Chen
(74) *Attorney, Agent, or Firm*—Perman & Green, LLP

(57) ABSTRACT

Manual actuating apparatus for operating a medical device includes a handle, a finger loop mounted on the handle for receiving the thumb of an operator, first and second lever members mounted on the handle for grasping engagement by fingers of the operator, at least one of the lever members and the finger loop being pivotally mounted on the handle for movement between first and second positions. A force transmitting member operably connects at least one of the finger loop and the first and second lever members for operating the medical device at a location distant from the handle such that, in the course of operating the medical device, the operator can reposition his fingers between the first and second lever members with rotation of his thumb within the finger loop and thereby assure a comfortable hand posture throughout the complete range of operation of the medical device.

8 Claims, 6 Drawing Sheets

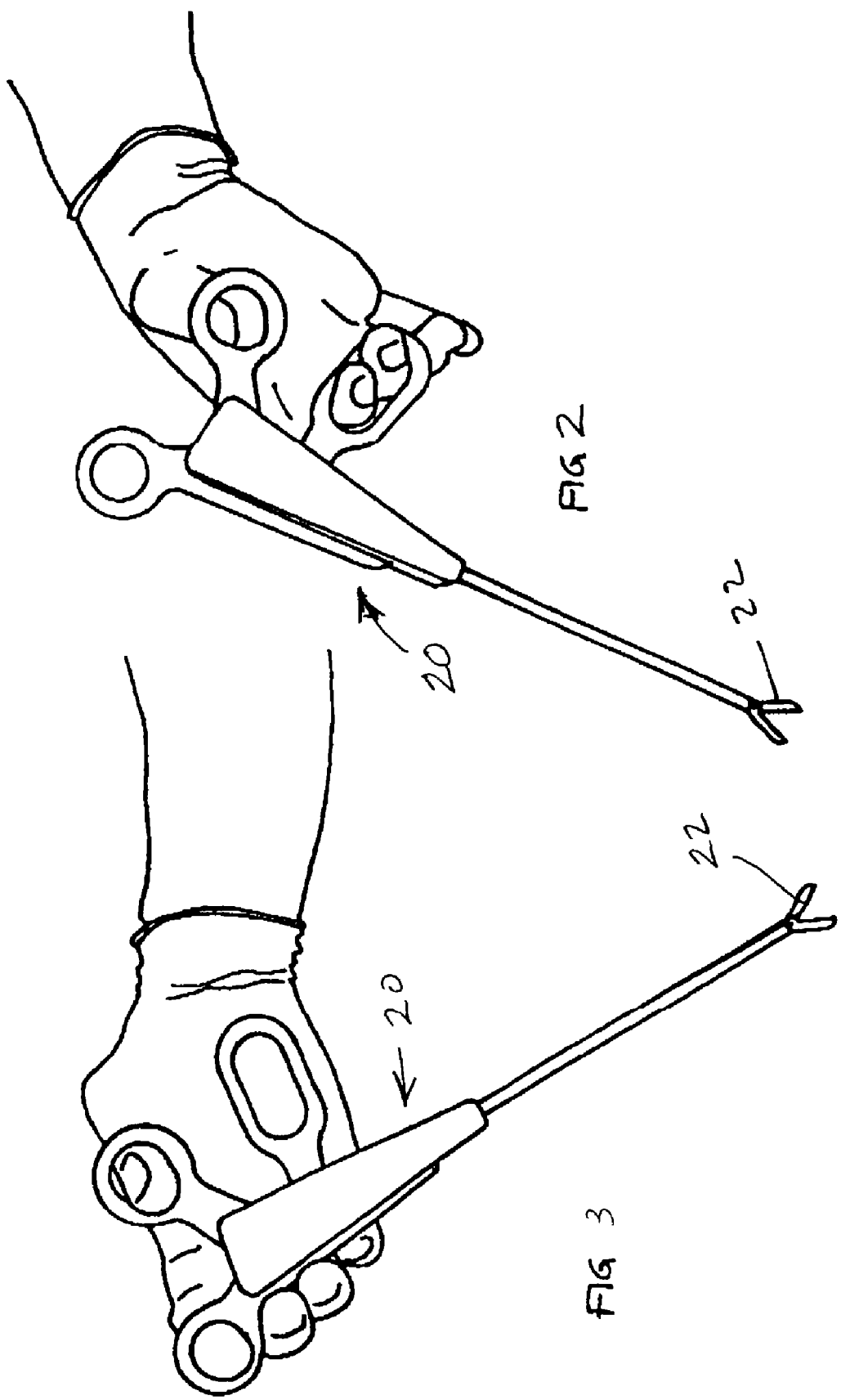

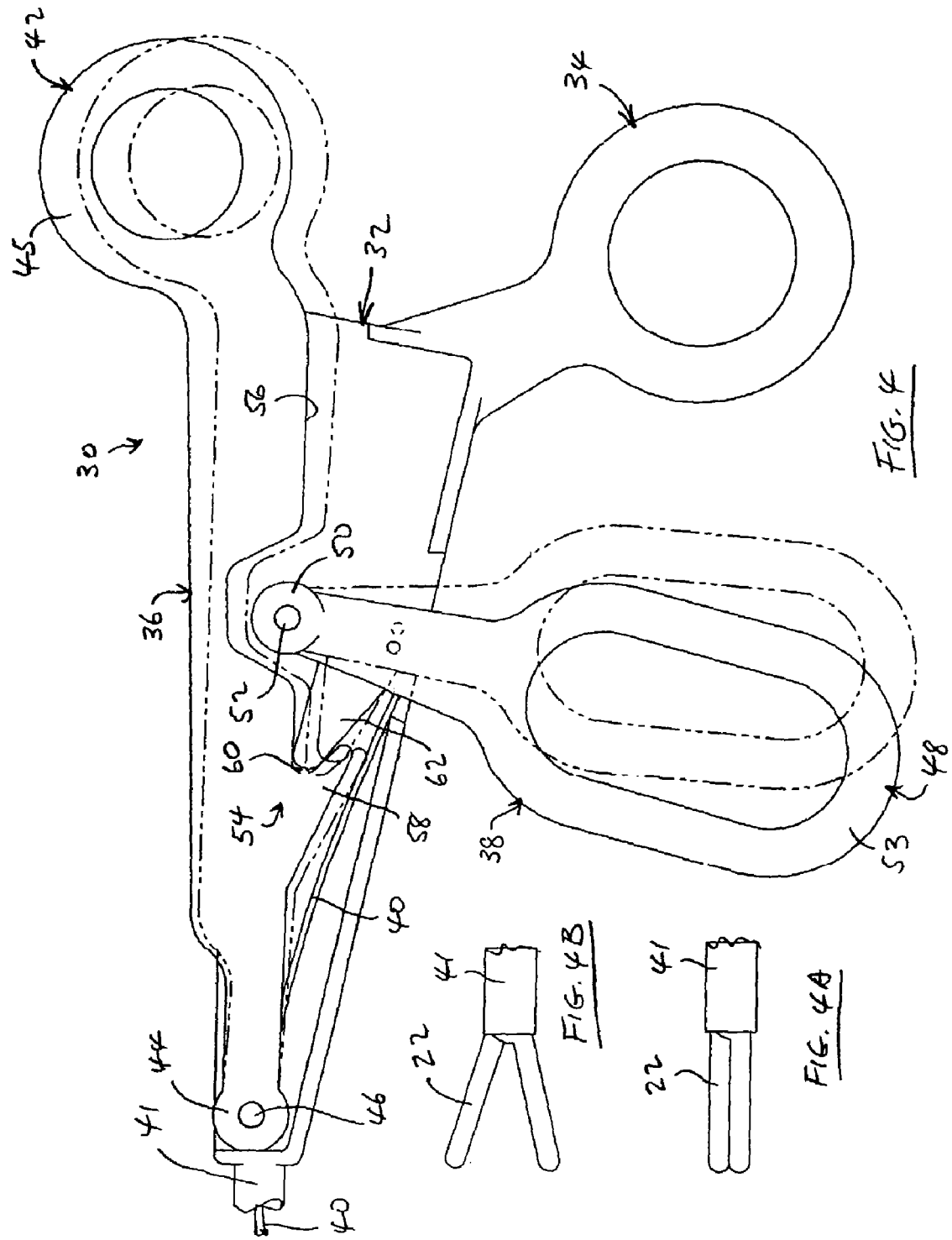

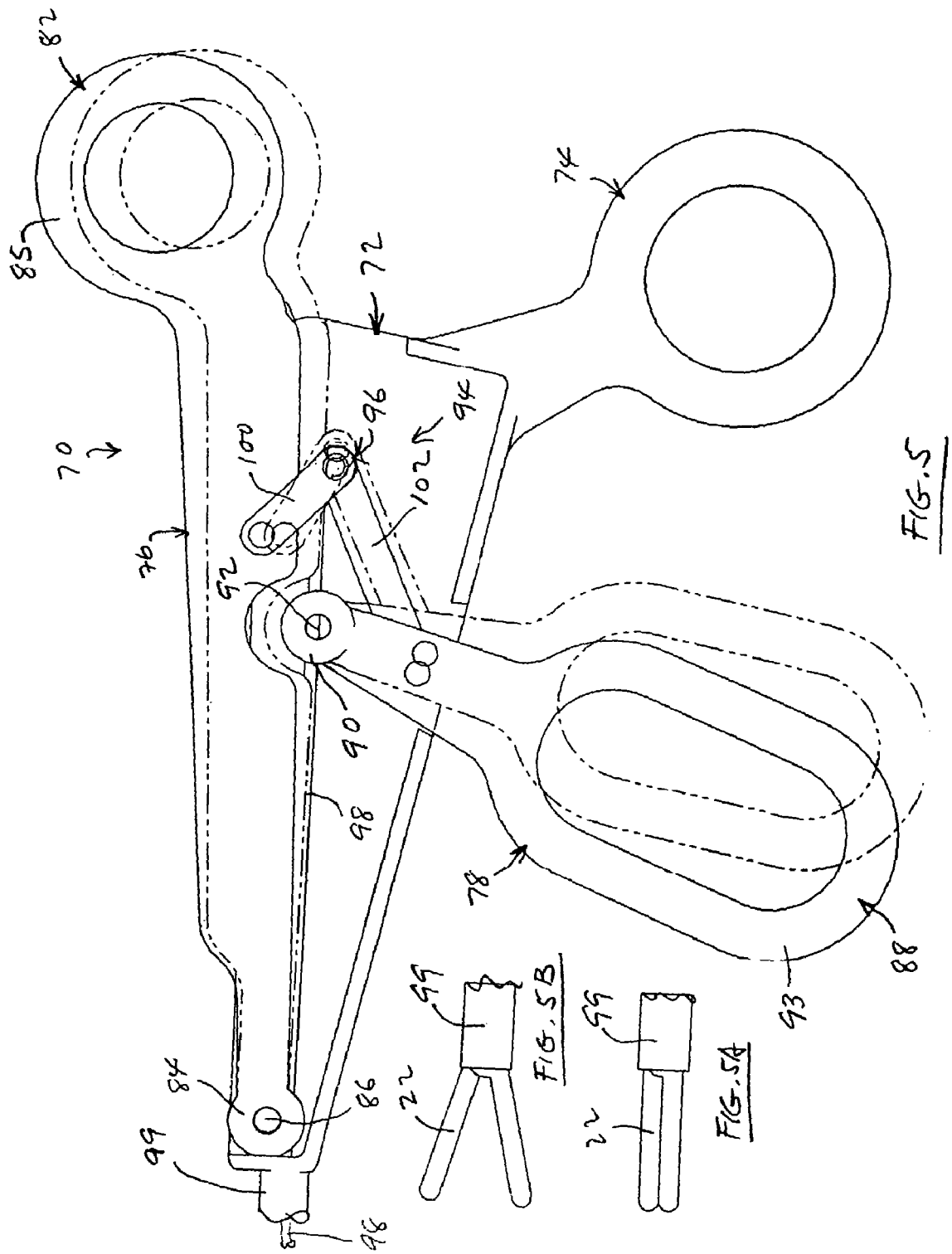

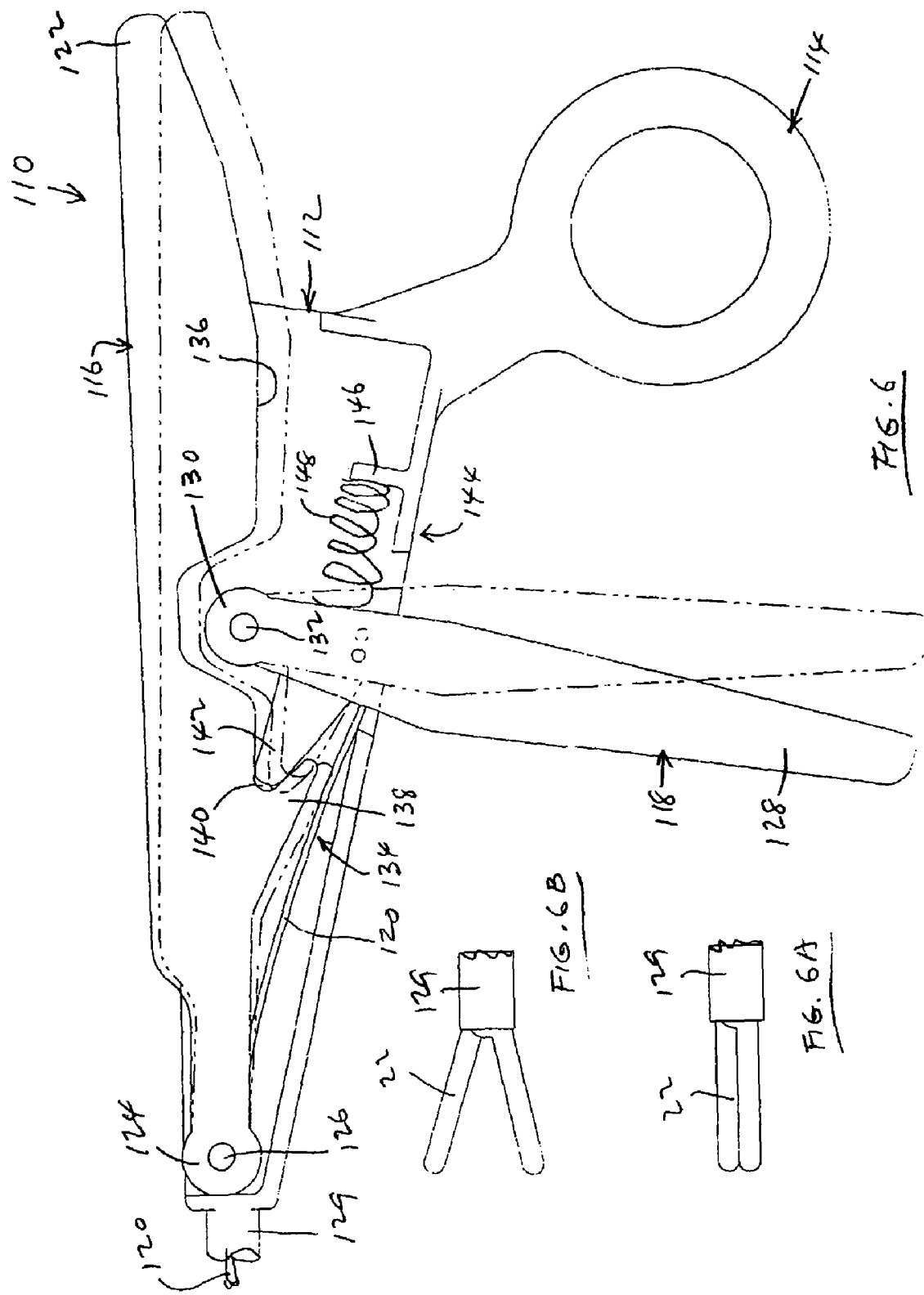

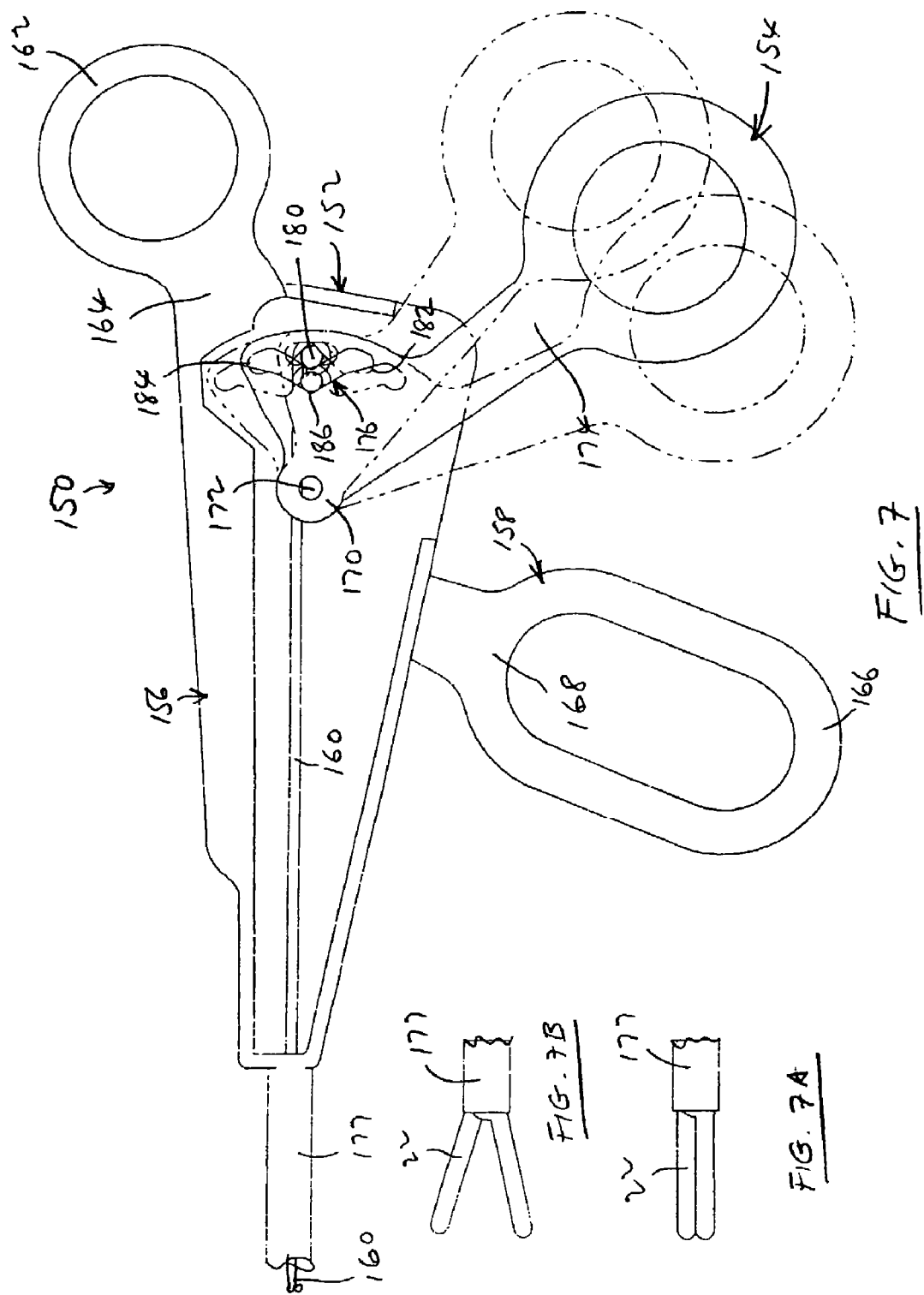

ENHANCED DEXTERITY SURGICAL HAND PIECE

This application claims the benefit of priority of U.S. Provisional Application Ser. No. 60/398,134 filed on Jul. 25, 2002.

BACKGROUND OF THE INVENTION

1. Field of the Invention

The present invention relates generally to manual actuating apparatus for operating a medical device and, more specifically, to such apparatus constructed to assure a comfortable hand posture for the operator throughout the complete range of operation of the medical device. The medical device may be, for example, a multifunctional minimally invasive surgical instrument.

2. Description of the Prior Art

Minimally invasive surgical procedures are being used with increasing regularity. These procedures are performed with minimally invasive surgical instruments which include a tool on the end of an elongated support tube opposite a handle. Access to the surgical site is provided by a trocar which is used to puncture and insert a cannula or hollow tube through the patient's skin and muscle tissue. The tool of the surgical instrument is positioned at the surgical site after being inserted through the cannula. The surgeon then manipulates a lever or other actuator on the handle to perform the surgical operation. This procedure is carried out while viewing the surgical site on a video monitor. Minimally invasive surgical procedures of this type offer substantial benefits to the patient in terms of reduced post-operative pain, reduced recovery time, and lower cost.

In a variety of medical devices used for a diversity of surgical or non-surgical procedures, devices are designed with a dedicated handle or proximal end and a distal or actuation end. Typically medical device handles prescribe how they will be held in the hand by the layout of their handle shape or position of finger loops. In instruments that contain loops, such as can be found in scissors type devices or grasping type devices, the loops are used for opening and closing the end effector, whether that is a scissors, grasper, clamp or similar device. In medical devices and more specifically minimally invasive or laparoscopic devices, a wide variety of angles of use can be generated. Typically a finger-looped device locks the fingers and hand into a single orientation that can only function comfortably across a limited range of angles. Both in angles distal or away from the user and oblique angles or angles acutely to the side of the user, devices with finger loops move beyond their effective comfort range and promote hand stress and fatigue. This stress and discomfort is the result of creating unnatural hand postures. These hand postures can create severe wrist adduction or flexion causing discomfort and a loss of strength or leverage to operate the device. In certain instruments such as instruments used for minimally invasive or laparoscopic dissection, a surgeon may operate a looped device for long periods of time, across a wide range of angles.

In most instances known to the inventor, when a handle for operating a medical device employs three or more finger or thumb elements, those elements in excess of the standard two for performing a certain function serve a different function. Typical examples of the prior art can be found in U.S. Pat. No. 6,299,625 to Bacher, No. 6,258,101 to Blake, III, No. 6,066,146 to Carroll et al., No. 5,456,684, and No. 5,376,094 to Kline. The noted condition for handles having multiple finger and thumb elements exists in each of these patented constructions.

It was with knowledge of the foregoing state of the technology that the present invention has been conceived.

SUMMARY OF THE INVENTION

Manual actuating apparatus for operating a medical device includes a handle, a finger loop mounted on the handle for receiving a finger of an operator, first and second lever members mounted on the handle for grasping engagement by fingers of the operator, at least one of the lever members and the finger loop being pivotally mounted on the handle for movement between first and second positions. A force transmitting member operably connects at least one of the finger loop and the first and second lever members for operating the medical device at a location distant from the handle such that, in the course of operating the medical device, the operator can reposition his fingers between the first and second lever members with rotation of his thumb within the finger loop and thereby assure a comfortable hand posture throughout the complete range of operation of the medical device.

In a preferred embodiment, the finger loop is integral with the handle and first and second lever members are pivotally attached to the handle, the second lever member being attached to the handle at a location intermediate a mounted end and a free end of the first lever member. The force transmitting member includes a pull rod attached to the second lever member intermediate its mounted and free ends and extends away from the finger loop and from the first and second lever members to the medical device at a distant location. An interengagement construction is provided between the lever members such that they move in a coordinated manner between the first and second positions. In this manner, with movement of the first and second lever members from initial positions farthest from the finger loop to extended positions nearest to the finger loop, the pull rod is drawn in a direction away from the medical device with appropriate actuation thereof in one manner and, with movement of the free ends of the lever members from their respective extended positions toward their initial positions, the pull rod is advanced in the direction toward the medical device with appropriate actuation thereof in an opposite manner.

In an alternate construction, both first and second lever members are integral with the handle and the finger loop is pivotally attached to the handle and is formed with a cam slot proximate its mounted end. A force transmitting member includes a pull rod with an integral cam follower at one end slidably received in the cam slot and extending in a direction away from the finger loop and from the lever members to the medical device at a distant location. The cam slot has opposed first and second ends and a neutral intermediate location and is shaped such that, when the cam follower is at the neutral intermediate location, the pull rod is drawn nearest to the medical device and such that when the finger loop is moved toward the first lever member, the cam follower moves in the cam slot to the first end and the pull rod is advanced in a direction away from the medical device with appropriate actuation thereof and such that when the finger loop is moved toward the second lever member, the cam follower moves in the cam slot through the neutral intermediate location to the second end and the pull rod is again drawn in a direction away from the medical device with appropriate actuation thereof.

The invention provides an alternative to the fixed hand position commonly used with medical device handles. The invention is comprised of a handle loop configuration for a particular handgrip position and an alternate control or finger loop, which allows the facilitation of a second hand grip position on the same device. In use, a finger such as the thumb is located in the center handle loop and acts as the stable connection to the instrument for axial positioning and also acts as a pivot point for moving the fingers from one hand posture to an alternate hand posture without letting go or loosing control of the device. The first hand posture grip is positioned for hand postures directly in front of the user. The alternate handgrip is to facilitate a comfortable hand posture at angles away or distal to the user, or oblique or acutely to the side of the user. The alternate grip provides increased comfort and greater hand leverage in activating the device by creating a more normal hand and wrist position. The surgeon can control his comfort level by alternating handle positions as needed.

A primary feature, then, of the present invention is the provision of manual actuating apparatus for operating a medical device and constructed to assure a comfortable hand posture for the operator throughout the complete range of operation of the medical device.

Another feature of the present invention is the provision of manual actuating apparatus for operating a medical device which includes a handle, a finger loop mounted on the handle for receiving a finger such as a thumb of an operator, first and second lever members mounted on the handle for grasping engagement by fingers of the operator, at least one of the lever members and the finger loop being pivotally mounted on the handle for movement between first and second positions, and a force transmitting member operably connecting at least one of the finger loop and the first and second lever members for operating the medical device at a location distant from the handle.

Yet another feature of the present invention is the provision of manual actuating apparatus for operating a medical device which has an interengagement construction between the first lever member and the second lever member such that the first and second lever members move in a coordinated manner between the first and second positions.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms.

Like numerals refer to like parts throughout the disclosure.

BRIEF DESCRIPTION OF THE DRAWINGS

FIG. 2 is a perspective view illustrating one mode of operation of the manual actuating apparatus illustrated in FIG. 1;

FIG. 3 is a perspective view illustrating another mode of operation of the manual actuating apparatus illustrated in FIG. 1;

FIG. 4 is a detail elevation view, certain parts being cut away and shown in section, of one embodiment of the manual actuating apparatus of the invention;

FIGS. 4A and 4B are detail views illustrating different positions of a medical device as operated by the manual actuating apparatus of FIG. 4;

FIG. 5 is a detail elevation view, certain parts being cut away and shown in section, of another embodiment of the manual actuating apparatus of the invention;

FIGS. 5A and 5B are detail views illustrating different positions of a medical device as operated by the manual actuating apparatus of FIG. 5;

FIG. 6 is a detail elevation view, certain parts being cut away and shown in section, of still another embodiment of the manual actuating apparatus of the invention;

FIGS. 6A and 6B are detail views illustrating different positions of a medical device as operated by the manual actuating apparatus of FIG. 6;

FIG. 7 is a detail elevation view, certain parts being cut away and shown in section, of yet another embodiment of the manual actuating apparatus of the invention; and FIGS. 7A and 7B are detail views illustrating different positions of a medical device as operated by the manual actuating apparatus of FIG. 7.

DETAILED DESCRIPTION OF THE PREFERRED EMBODIMENTS

Figure 1:
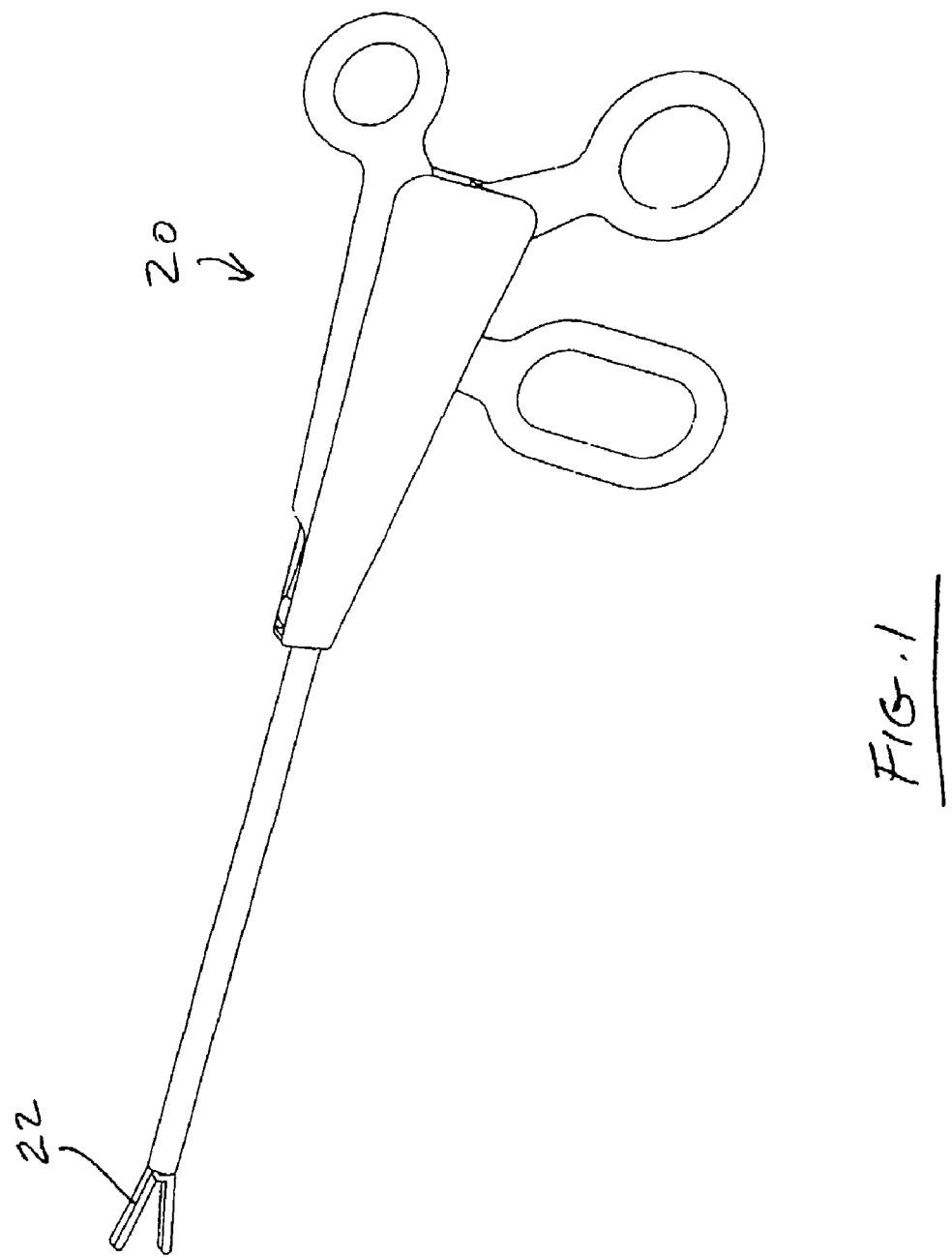
FIG. 1 is a diagrammatic perspective view illustrating manual actuating apparatus embodying the invention operating a medical device.

Turn now to the drawings and, initially, to FIG. 1 which generally illustrates manual actuating apparatus 20 for operating a medical device 22 designed to offer a surgeon increased comfort, dexterity, and leverage during both manipulation and actuation of the device in situ. With laproscopic devices in particular, the apparatus 20 allows the surgeon an optional hand position designed to eliminate extreme wrist postures while increasing available leverage. The actuating apparatus 20 of the invention transitions between hand positions without loss of device control by means of a stationary finger pivot. This feature allows a change in grip without being released from the medical device 22 or losing axial positioning.

FIG. 2 illustrates a normal wrist position and extension and applied to the manual actuating apparatus 20 in the manner used with known apparatus. FIG. 3 illustrates an alternate hand position, using the manual actuating apparatus 20, which offers a user an optimal wrist position to relieve wrist stress.

A summary of the features of the invention may be expressed as follows:
  a provision for multiple hand positions to reduce stress, discomfort, and fatigue of the hand and wrist muscles of the user;
  provides for increased leverage for actuating devices at oblique device angles;
  employs a finger pivot system to facilitate a change in hand position without losing control of the device;
  combines two conventional instrument grips familiar to surgeons, the so-called laproscopic grip and the hemostat grip; and
  may reduce the occurrence of repetitive stress injuries.

A first embodiment of the invention will now be described with the aid of FIG. 4. In this instance, manual actuating apparatus 30 for operating a medical device 22 (of any appropriate nature as typically illustrated in FIGS. 1-3) includes a handle 32, a finger loop 34 integral with the handle for receiving a finger, such as for example the thumb of an operator, and first and second lever members, 36, 38, respectively, mounted on the handle for grasping engagement by fingers of the operator. The finger loop 34 is generally adapted to receive any suitable finger of the operator that facilitates a change in hand position without losing control of the device. In one embodiment, and as will be referred to further herein, the thumb of the operator is received in the finger loop, although any suitable finger can be used, other than including the thumb. The lever members 36, 38 are pivotally mounted on the handle 32 for movement between first solid-line and second dashed-line positions. A force transmitting member termed a pull rod 40 extends away from the finger loop 34 and from the lever members 36, 38 and, passing through a guide cannula 41, operably connects the second lever member 38 to the medical device 22 for operating the medical device which is located distant from the handle.

While termed a pull rod, the force transmitting member may be of any suitable construction including, by way of example, wire, chain, a linkage, and the like. In any event, in the course of operating the medical device, the operator can reposition his fingers between the first and second lever members with rotation of his thumb within the finger loop 34, which can also be referred to as a thumb loop when the thumb is used, and thereby assure a comfortable hand posture throughout the complete range of operation of the medical device.

As clearly seen in FIG. 4, the first lever member 36 extends between a free end 42 and a mounted end 44 pivotally attached, as by pin 46, to the handle 32. An upper finger loop 45 is integral with the first lever member at the free end 42. The second lever member 38 also extends between a free end 48 and a mounted end 50 pivotally attached, as by a pin 52, to the handle 32 at a location intermediate the mounted end 44 and the free end 42 of the first lever member 36. A front finger loop 53 is integral with the second lever member 38 at its free end 48.

Also as seen in FIG. 4, an interengagement construction 54 is provided between the lever members 36 and 38 such that they move in a coordinated manner between the first and second positions. In actual fact, the interengagement construction includes an elongated side 56 on the lever member 36 and a first nose member 58 which projects acutely away from the elongated side toward the lever member 38 and intermediate the mounted end 44 and the free end 42 of the lever member 36. The elongated side 56 and the nose member 58 together define a recess 60. A second nose member 62 on the second lever member 38 extends away from the second lever member intermediate the mounted and free ends, 50 and 48, respectively, and projects into the recess 60 and the nose members and the elongated side 56 of the lever member 36 are mutually slidably engageable. In this manner, with movement of the lever members 36, 38 from their initial positions farthest from the finger loop 34 to extended positions nearest to the finger loop, the first nose member 58 slidably engages with the second nose member 62 and causes movement of the free ends 42, 48 of the lever members from their initial solid-line positions to their extended dashed-line positions with the result that the pull rod 40 is drawn in a direction away from the medical device 22 with appropriate actuation of the medical device in one particular manner (see FIG. 4A). In an opposite manner, with movement of the free ends of the lever members from their extended positions toward their initial positions, the pull rod is advanced in the direction toward the medical device, again, with its appropriate actuation thereof in another particular manner (see FIG. 4B).

Another embodiment of the invention will now be described with the aid of FIG. 5. In this instance, manual actuating apparatus 70 for operating a medical device 22 includes a handle 72, a finger loop 74 integral with the handle for receiving a finger, such as for example the thumb of an operator, and first and second lever members, 76, 78, respectively, mounted on the handle for grasping engagement by fingers of the operator. As in the earlier-described embodiment, the lever members 76, 78 are pivotally mounted on the handle 72 for movement between first solid-line and second dashed-line positions.

Again, as clearly seen in FIG. 5, the first lever member 76 extends between a free end 82 and a mounted end 84 pivotally attached, as by pin 86, to the handle 72. An upper finger loop 85 is integral with the first lever member at the free end 82. The second lever member 78 also extends between a free end 88 and a mounted end 90 pivotally attached, as by a pin 92, to the handle 72 at a location intermediate the mounted end 84 and the free end 82 of the first lever member 76. A front finger loop 93 is integral with the second lever member 78 at its free end 88.

Also as seen in FIG. 5, an interengagement construction 94 is provided between the lever members 76 and 78 such that they move in a coordinated manner between the first solid-line position and the second dashed-line position. In actual fact, the interengagement construction 94 includes a linkage 96 between the first lever member 76 and the second lever member 78 such that the lever members move in a coordinated manner between the first and second positions. As in the earlier described embodiment, the force transmitting member includes a pull rod 98 attached to the linkage 96 and extends away from the finger loop 74 and away from the first and second lever members to the medical device 22 at a distant location. More specifically, the linkage 96 includes a first link 100 pivotally attached to the first lever member 76 and a second link 102 pivotally attached at one end to the second lever member 78 and at its opposite end to the first link away from the first lever member 76. The pull rod 98 is pivotally attached to the linkage 96.

In a manner similar to the operation of the first embodiment, with movement of the first and second lever members 76, 78 from their initial positions to their extended positions, the pull rod is drawn through a guide cannula 99 in a direction away from the medical device 22 with appropriate actuation thereof in one manner (see FIG. 5A) and with movement of the free ends of the lever members 76, 78 from their extended positions toward their initial positions, the pull rod is advanced in the direction toward the medical device with its appropriate actuation in another manner (see FIG. 5B).

Still another embodiment of the invention will now be described with the aid of FIG. 6. In this instance, manual actuating apparatus 110 for operating a medical device 22 includes a handle 112, a finger loop 114 integral with the handle for receiving, for example, the thumb of an operator, and first and second lever members 116, 118, respectively, mounted on the handle for grasping engagement by fingers of the operator. The lever members 116, 118 are pivotally mounted on the handle 112 for movement between first solid-line and second dashed-line positions. A pull rod 120 extends away from the finger loop 114 and from the lever members 116, 118 and operably connects the second lever member 118 to the medical device 22 for operating the medical device which is located distant from the handle.

As clearly seen in FIG. 6, the first lever member 116 extends between a free end 122 and a mounted end 124 pivotally attached, as by pin 126, to the handle 112. The second lever member 118 also extends between a free end 128 and a mounted end 130 pivotally attached, as by a pin 132, to the handle 112 at a location intermediate the mounted end 124 and the free end 122 of the first lever member 116.

Also as seen in FIG. 6, an interengagement construction 134 is provided between the lever members 116. and 118 such that they move in a coordinated manner between the first and second positions. In actual fact, as in an earlier embodiment, the interengagement construction 134 includes an elongated side 136 on the lever member 116 and a first nose member 138 which projects acutely away from the elongated side toward the lever member 118 and intermediate the mounted end 124 and the free end 122 of the lever member 116. The elongated side 136 and the nose member 138 together define a recess 140. A second nose member 142 on the second lever member 118 extends away from the second lever member intermediate the mounted and free ends., 130 and 128, respectively, and projects into the recess 140 and the nose members and the elongated side 136 of the lever member 116 are mutually slidably engageable. In this manner, with movement of the lever members 116, 118 from their initial positions to their extended positions, the first nose member 138 slidably engages with the second nose member 142 and causes movement of the free ends 122, 128 of the lever members from their initial solid-line positions to their extended dashed-line positions with the result that the pull rod 120 is drawn through a cannula 129 in a direction away from the medical device 22 with appropriate actuation of the medical device in one particular manner (see FIG. 6A). In an opposite manner, with movement of the free ends of the lever members from their extended positions toward their initial positions, the pull rod is advanced in the direction toward the medical device, again, with its appropriate actuation thereof in another particular manner (see FIG. 6B).

A resilient actuator 144 serves to bias the lever members 116, 118 toward their initial positions, respectively, while, with movement of the lever members from their initial positions to their extended positions, the pull rod 120 is drawn in a direction away from the medical device 22 with appropriate actuation thereof in one manner and, with movement of the free end of the first and second lever members from their respective extended positions toward their respective initial positions, the pull rod is advanced in the direction toward the medical device with its appropriate actuation in an opposite manner. More specifically, the resilient actuator 144 includes a bracket 146 fixed on the handle spaced from the second lever member 118 in the direction of the finger loop 114. A compression spring 148 extends between, and is fixed at its opposite ends, respectively, to the second lever member 118 and to the bracket 146.

Yet another embodiment of the invention will now be described with the aid of FIG. 7. In this instance, manual actuating apparatus 150 includes a handle 152, a finger loop 154 mounted on the handle for receiving a finger such as the thumb of an operator, and first and second lever members, 156, 158, respectively, mounted on the handle for grasping engagement by fingers of the operator. In this instance, the finger loop 154 is pivotally mounted on the handle 152 for movement between a first solid-line position and a second dashed-line position. A pull rod 160 operably connects the finger loop to the medical device 22 for operating the medical device at a location distant from the handle.

Again, in this instance, both the first lever member 156 and the second lever member 158 are integral with the handle 152. An upper finger loop 162 is integral with the first lever member at a free end 164 and a front finger loop 166 is integral with the second lever member at a free end 168. The finger loop 154 extends between a mounted end 170 pivotally attached to the handle 152 by way of pin 172 and a free end 174 and a cam slot 176 is formed in the finger loop 154 proximate the mounted end 170.

The pull rod 160 has an integral cam follower 180 at one end which is slidably received in the cam slot 176 and the pull rod extends in a direction away from the finger loop 154 and from the first and second lever members 156, 158, respectively, through a guide cannula 177 to the medical device 22 at a distant location. The cam slot 176 has opposed first and second ends 182, 184, respectively, and a neutral intermediate location 186 and is shaped such that, when the cam follower 180 is at the neutral intermediate location 186, the pull rod 160 is drawn nearest to the medical device 22 and such that when the finger loop 154 is moved toward the first lever member 156, the cam follower moves in the cam slot to the first end 182 and the pull rod is advanced in a direction away from the medical device 22 with appropriate actuation thereof (see FIG. 7A) and such that when the finger loop 154 is moved toward the second lever member 158, the cam follower moves in the cam slot through the neutral intermediate location 186 to the second end 184 and the pull rod is again drawn in a direction away from the medical device for its appropriate actuation (see FIG. 7B).

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. Manual actuating apparatus for operating a medical device having a common closable jaw for effecting operation of the medical device comprising:
 a handle;
 a finger loop mounted on the handle for receiving a finger of an operator;
 first and second lever members mounted on the handle for grasping engagement by other fingers of the operator, each of the first and second lever members being independently and pivotably mounted on the handle for movement between respective first and second positions wherein the first lever member extends between a mounted end pivotally attached to the handle and a free end and wherein the second lever member extends between a free end and a mounted end pivotally attached to the handle at a location intermediate the mounted end and the free end of the first lever member;
 an interengagement construction between the first lever member and the second lever member such that movement of one of the first or second lever members causes movement of the other one of the first or second lever member such that the first and second lever members move in a coordinated manner between the first and second positions; and
 a force transmitting member operably connecting at least one of the finger loop and the first and second lever members to the common closable jaw of the medical device for operating the common closable jaw at a location distant from the handle where movement of the first and second lever members between the first and second positions, relative to the finger loop, causes movement of the common closable jaw for opening and closing the common closable jaw of the medical device;
 whereby, in the course of operating the common closable jaw, the first and second lever members are positioned relative to the finger loop so that the operator can reposition the other fingers between the first and second lever members with rotation of the finger within the finger loop while operating the common closable jaw with the finger within the finger loop and thereby assure a comfortable hand posture throughout the complete range of operation of the medical device.

2. Manual actuating apparatus as set forth in claim 1 wherein the finger loop is integral with the handle; and wherein the force transmitting member includes a pull rod attached to the second lever member intermediate the mounted end and the free end and extending away from the finger loop and the first and second lever members to the common closable jaw distant therefrom; and whereby, with movement of the first and second lever members from initial positions farthest from the finger loop to extended positions nearest to the finger loop, the pull rod is drawn in a direction away from the common closable jaw with appropriate actuation thereof in one manner; and whereby, with movement of the free ends of the first and second lever members from their respective extended positions toward their initial positions, the pull rod is advanced in the direction toward the common closable jaw with appropriate actuation thereof in an opposite manner.

3. Manual actuating apparatus as set forth in claim 2 wherein the interengagement construction includes:

an elongated side on the first lever member and a first nose member projecting acutely away therefrom toward the second lever member and intermediate the mounted end and the free end, the elongated side and the first nose member together defining a recess;

a second nose member on the second lever member extending away therefrom intermediate the mounted end and the free end and projecting into the recess of the first lever member, the first and second nose members and the elongated side of the first lever member being mutually slidably engageable;

whereby, with movement of the first and second lever members from initial positions farthest from the finger loop to extended positions nearest to the finger loop, the first nose member slidably engages with the second nose member and causes movement of the free ends of the lever members from the initial positions to the extended positions, the pull rod is drawn in a direction away from the medical device with appropriate actuation thereof in one manner; and whereby, with movement of the free ends of the first and second lever members from their extended positions toward their initial positions, the pull rod is advanced in the direction toward the common closable jaw of the medical device with appropriate actuation thereof in an opposite manner.

4. Manual actuating apparatus as set forth in claim 1 wherein an upper finger loop is integral with the first lever member at the free end thereof; and wherein a front finger loop is integral with the second lever member at the free end thereof.

5. Manual actuating apparatus as set forth in claim 1 wherein the finger loop is integral with the handle; and
wherein the interengagement construction includes:

a linkage between the first lever member and the second lever member such that the first and second lever members move in a coordinated manner between the first and second positions; and the force transmitting member including a pull rod attached to the linkage and extending away from the finger loop and away from the first and second lever members to the common closable jaw distant therefrom;

whereby, with movement of the first and second lever members from initial positions farthest from the finger loop to extended positions nearest to the finger loop, the pull rod is drawn in a direction away from the common closable jaw with appropriate actuation thereof in one manner; and whereby, with movement of the free ends of the first and second lever members from their extended positions toward their initial positions, the pull rod is advanced in the direction toward the common closable jaw with appropriate actuation thereof in another manner.

6. Manual actuating apparatus as set forth in claim 5 wherein the linkage includes:

a first link pivotally attached to the first lever member; and a second link pivotally attached at one end to the second lever member and at its opposite end to the first link away from the first lever member; and wherein the pull rod is pivotally attached to the linkage.

7. Manual actuating apparatus as set forth in claim 1 wherein the finger loop is integral with the handle; and wherein the force transmitting member includes a pull rod attached to the second lever member intermediate the mounted end and the free end and extending away from the finger loop and the first and second lever members to the common closable jaw of the medical device distant therefrom; and including:

a resilient actuator biasing the first and second lever members toward initial positions, respectively;

whereby, with movement of the first and second lever members from their initial positions farthest from the finger loop to extended positions nearest to the finger loop, the pull rod is drawn in a direction away from the common closable jaw of the medical device with appropriate actuation thereof in one manner; and whereby, with movement of the free end of the first and second lever members from their respective extended positions toward their respective initial positions, the pull rod is advanced in the direction toward the common closable jaw of the medical device with appropriate actuation thereof in an opposite manner.

8. Manual actuating apparatus as set forth in claim 7 wherein the resilient actuator includes:

a bracket fixed on the handle spaced from the second lever member in the direction of the finger loop; and a compression spring extending between and fixed at its opposite ends, respectively, to the second lever member and to the bracket.

* * * * *